US010709723B2

(12) United States Patent
Deboeck et al.

(10) Patent No.: US 10,709,723 B2
(45) Date of Patent: Jul. 14, 2020

(54) PHARMACEUTICAL ANTI-INFECTIVE COMPOSITION FOR INHALATION

(71) Applicants: Arthur M. Deboeck, Gurabo, PR (US); Phillipe Baudier, Brussels (BE); Francis Vanderbist, Brussels (BE)

(72) Inventors: Arthur M. Deboeck, Gurabo, PR (US); Phillipe Baudier, Brussels (BE); Francis Vanderbist, Brussels (BE)

(73) Assignee: GALEPHAR PHARMACEUTICAL RESEARCH, INC., Juncos, PR (US)

(*) Notice: Subject to any disclaimer, the term of this patent is extended or adjusted under 35 U.S.C. 154(b) by 0 days.

(21) Appl. No.: 15/436,242

(22) Filed: Feb. 17, 2017

(65) Prior Publication Data
US 2017/0232029 A1 Aug. 17, 2017

Related U.S. Application Data

(63) Continuation of application No. 14/521,000, filed on Oct. 22, 2014, now abandoned, which is a continuation of application No. 13/137,826, filed on Sep. 15, 2011, now abandoned, which is a continuation of application No. 12/385,518, filed on Apr. 9, 2009, now abandoned, which is a continuation of application No. PCT/EP2007/060855, filed on Oct. 11, 2007, now abandoned.

(30) Foreign Application Priority Data

Oct. 11, 2006 (WO) ............... PCT/EP2006/000112

(51) Int. Cl.
| | |
|---|---|
| *A61K 31/7052* | (2006.01) |
| *A61K 31/7032* | (2006.01) |
| *A61P 31/04* | (2006.01) |
| *A61K 31/7036* | (2006.01) |
| *A61K 31/7048* | (2006.01) |
| *A61K 9/00* | (2006.01) |
| *A61K 47/26* | (2006.01) |
| *A61K 9/48* | (2006.01) |
| *A61K 47/18* | (2017.01) |
| *A61K 47/24* | (2006.01) |
| *A61K 47/28* | (2006.01) |

(52) U.S. Cl.
CPC ........ *A61K 31/7052* (2013.01); *A61K 9/0073* (2013.01); *A61K 9/0075* (2013.01); *A61K 9/0078* (2013.01); *A61K 9/4816* (2013.01); *A61K 31/7032* (2013.01); *A61K 31/7036* (2013.01); *A61K 31/7048* (2013.01); *A61K 47/183* (2013.01); *A61K 47/24* (2013.01); *A61K 47/26* (2013.01); *A61K 47/28* (2013.01); *A61P 31/04* (2018.01)

(58) Field of Classification Search
None
See application file for complete search history.

(56) References Cited

U.S. PATENT DOCUMENTS

| 4,379,781 A | 4/1983 | Hull |
|---|---|---|
| 2004/0142026 A1 | 7/2004 | Boni |

FOREIGN PATENT DOCUMENTS

| EP | 0032304 A1 | 7/1981 |
|---|---|---|
| WO | WO 02/03998 | 1/2002 |
| WO | WO 2004/075874 | 9/2004 |
| WO | WO 2005/110022 A2 | 11/2005 |
| WO | WO 2006/002178 | 1/2006 |
| WO | WO 2008/025560 | 3/2008 |

OTHER PUBLICATIONS

Hermann, T., "Aminoglycoside antibiotics: old drugs and new therapeutic approaches" Cell Mol Life Sci vol. 64 pp. 1841-1852 (Year: 2007).*
Bahal et al., "The New Macrolide Antibiotics: Azithromycin, Clarithromycin, Dirithromycin, Androxithromycin" The Annals of Pharmacotherapy vol. 26 pp. 46-55 (Year: 1992).*
Jabra-Rizk et al., "Fungal Biofilms and Drug Resistance" Emerging Infectious Diseases vol. 10 No. 1 pp. 14-19 (Year: 2004).*
Thoulouze et al., "Can viruses form biofilms?" Trends in Microbiology vol. 19 No. 6 pp. 257-262 (Year: 2011).*
Goto et al., "Bacterial biofilms and catheters in experimental urinary tract infection" International Journal of Antimicrobial Agents vol. 11 pp. 227-231 (Year: 1999).*
Clark, Aerosol Science and Technology, 1995, 22, pp. 374-391.
The United States Pharmacopeia, National Formulary, USP 24 NF 19, United States Pharmacopeial Convention, Inc. 2000, pp. 2404-2406.
Goto, et al., International Journal of Antimicrobial Agents, 1999, pp. 227-231.
Gennaro, A.R., Remington: The Science and Practice of Pharmacy, 19th edition, 1995, pp. 1395, 1397, 1462 and 1615, Mack Publishing.
"Definition of Derivative", retrieved from Merriam-Webster online dictionary <<http://www.merriamwebster.com/dictionary/.
Conway, S. P. et al., "Optimizing treatment policies and improving care: impact on outcome in patients with cystic fibrosis" Expert Rev. Pharmacoecon. Outcomes Res. Dec. 2005: 5 (6): 791-806 (Abstract).
Wroblewska, Marta. "Novel Therapies of multidrug-resistant *Pseudomonas aeruginosa* and *Acinetobacter* ssp. infections: the state of the art" Archivum Immunologiae et Therapiae Experimentalis Apr. 2006, vol. 54, Issue 2, pp. 113-120 (Abstract).
Saiman, Lisa et al. "Synergistic Activities of Macrolide Antibiotics against Pseudomonas aeruginosa, Burkholderia cepacia, Stenotrophomonas maltophilia, and Alcaligenes xylosoxidans isolated from patients with Cystic Fibrosis" Antimicrob. Agents Chemother. Apr. 2002; 46(4): 1105-1107.

(Continued)

*Primary Examiner* — Eric Olson
(74) *Attorney, Agent, or Firm* — Juneau & Mitchell; William E. Beaumont (57) ABSTRACT

An anti-infective composition for inhalation, containing, at least an effective amount of an antimicrobial aminoglycoside compound or a salt thereof; and an effective amount of a biofilm modifier which is a macrolide compound or salt thereof.

21 Claims, 1 Drawing Sheet

(56) References Cited

OTHER PUBLICATIONS

Touw, D.J. et al. "Inhalation of antibiotics in cystic fibrosis", Eur. Respir. J., 1996, B, 1594-1604.

* cited by examiner

PHARMACEUTICAL ANTI-INFECTIVE COMPOSITION FOR INHALATION

FIELD OF THE INVENTION

The invention relates to pharmaceutical compositions for the treatment of lung infections caused by biofilm producing bacterial, fungal or viral pathogens.

The invention discloses inhaled combinations of at least one antibiotic agent which is an aminoglycoside or a salt thereof and at least one biofilm modifyer agent which is a macrolide or a salt thereof, for the treatment of recurrent lung infections associated with a biofilm.

The compositions of the present invention are meant to be administered locally in the lungs of patients, said lung administration being performed using a dry powder inhaler system or a nebulizer.

The weight ratio of each of said antibiotic and said biofilm modifyer may be superior or equal to 10% of said dry powder inhaler. The weight ratio between the aminoglycoside and the macrolide in the compositions of the invention can be comprised between 0.2 and 5, and the total amount of both active ingredients per pharmaceutical composition can be comprised between 1 and 50 mg for a total weight of dry powder per composition being comprised between 1 and 100 mg.

BACKGROUND OF THE INVENTION

Antibiotic resistance and persistent infections refractory to per os or injected treatments are a major problem in bacteriological transmissions, resistance to eradication and ultimately pathogenesis. While the consequences of bacterial resistance and bacterial recalcitrance are the same, there are two different mechanisms that explain the two processes.

Antibiotic/Antimicrobial Resistance. In the case of antibiotic or antimicrobial resistance, biofilms provide the unique opportunity for bacterial to reside in close proximity with one another for long periods of time. This prolonged juxtaposition of bacterial allows gene transfer between and among bacteria, allowing the genes of resistance to be transferred to same or different strains of bacteria to neighboring cells that are not resistant. Consequently, a virulent cell can transfer its virulence genes to a non-virulent cell, making it resistant to antibiotics.

Antibiotic/Antimicrobial Recalcitrance. In the case of antibiotic or antimicrobial recalcitrance, there are two possible explanations, both of which involve the biofilm and both of which may be operative simultaneously. While gene transfer may occur, it is not a factor in recalcitrance.

Biofilms are matrix-enclosed accumulations of microorganisms such as bacteria (with their associated bacteriophages), fungi, protozoa and viruses that may be associated with these elements. While biofilms are rarely composed of a single cell type, there are common circumstances where a particular cellular type predominates.

Biofilms are the most important primitive structure in nature. In a medical sense, biofilms are important because the majority of infections that occur in animals are biofilm-based. Infections from planktonic bacteria, for example, are only a minor cause of infectious disease.

In summary, the biofilm formation consists of planktonic cells adsorbing onto a surface, experience phenotypic transformations and form colonies. Once the colonizing cells become established, they secrete exopolysaccharides that serve as the backbone for the growing biofilm. While the core or backbone of the biofilm is derived from the cells themselves, other components e.g., lipids, proteins etc, over time, become part of the biofilm. Thus a biofilm is heterogeneous in its total composition, homogenous with respect to its backbone and heterogeneous with respect to its depth, creating diffusion gradients for materials and molecules that attempt to penetrate the biofilm structure.

The first of the explanatory mechanisms of resistance offered by biofilm is simply a physical phenomenon: the biofilm structures present a barrier to the penetration of antibiotics and antimicrobial agents and a protective shroud to physical agents such as ultraviolet radiation.

Another biofilm resistance mechanism is based on biochemical or metabolic principles. Just as the deep-seated bacterial are protected from chemical and physical agents by the "barrier" effect of the biofilm, the biofilm also acts as a barrier to nutrients that are necessary for normal metabolic activity. Further, the nutrient-limited bacteria are in a reduced state of metabolic activity, which make them less susceptible to chemical and physical agents because the maximal effects of these killing agents are achieved only when the bacteria are in a metabolically active state. In addition, biofilms are linked to other virulence factors of pathogens (like efflux pumps or alginate secretion).

In particular, biofilms constitute a growing problem for the treatment of respiratory diseases associated with infection like cystic fibrosis, diffuse panbronchiolitis, exacerbation of chronic obstructive pulmonary diseases, pneumonia, etc. . . . The treatments of those diseases with antibiotics become consequently more and more difficult due to the resistance offered by said biofilm.

Biofilms are associated with various bacteria, fungi and viruses among which *Pseudomonas aeruginosa* and *Staphylococcus aureus* cause the most dramatical consequences in the above cited respiratory diseases.

Whichever the mechanistic explanations for either resistance or recalcitrance, the removal or disruption of the biofilm is a mandatory requirement for the successful treatment of the infection.

Aminoglycoside antibiotics are very active antimicrobial agents but their use has been limited because of their high frequence of serious and irreversible adverse events associated with their use. The most common and important toxicity are nephrotoxicity and ototoxicity. Aminoglycosides are usually administered by intra-venous injection because they are very poorly absorbed by the oral route. Nevertheless, a nebulized formulation of Tobramycin (TORI®) to treat lung infections due to *P. aeruginosa* in Cystic Fibrosis patients is available.

TOBI® presents the advantage to allow to treat lung infections locally with a lower systemic exposure than the intravenous formulation and is thus responsible of less side-effects. However, due to low respiratory fraction compositions administered through nebulisation (5 to 8% of the nominal dose), the nominal dose to administer (300 mg of Tobramycin b.i.d.) is still too high and can be responsible of a significant frequency and/or severity of side-effects.

Although, aminoglycoside antibiotics are very effective against several planktonic bacteria, they are much less effective if not ineffective against the same bacterial which have formed a biofilm. This phenomenon of resistance of biofilms is also true for other antibiotics and represents a major public health concern. In some specific lung diseases like cystic fibrosis and diffuse panbronchiolitis, it is of major importance to dispose of compositions which are able to destroy, disorganize, inhibit the biofilm and/or able to prevent its formation.

Oral dosage formulations of macrolides antibiotics are widely used to treat, among others, respiratory infections like acute exacerbations of chronic bronchitis, sinusitis, rhinopharyngitis, . . .

While macrolides antibiotics are mostly available as oral dosage forms containing several hundreds of milligrams of the antibiotic, no inhaled form has been available up to now, because amounts of hundreds of mg are impossible to administer ambulatorily by inhalation through systems like dry powder inhalers or metered dose inhalers.

In summary, oral and intravenous antibiotic compositions used to treat bacterial infections are efficient not and safe against bacterial biofilms responsible for lung infections or surinfections.

Consequently, there is an urgent need for efficient and safe antibiotic compositions, administered directly in the lung and able to treat lung infections due to biofilms. The present invention discloses a dry powder composition for inhalation allowing to obtain a) a high pulmonary amount of aminoglycoside antibiotic and b) high dose of a biofilm modifier which is selected from the group of macrolides and derivatives, which is efficacious against said biofilm when administered directly into the lungs.

State of the Art

Several inventors have already described attempts to act on bacterial biofilms.

JP 726 7868 relates to a biofilm-removing agent containing a macrolide antibiotic at a low concentration, capable of removing biofilm formed by periodontal pathogens, making a drug effectively penetrate to and act on an affected part and also suppressing the formation of the biofilm and useful for self care. This is a removing agent of biofilm periodontal pathogens containing a macrolide antibiotic having a 14-membered ring, preferably belonging to an erythromycin, a clarithromycin, a triacetyloleandomycin or a roxithromycin. For administration, the antibiotic may be contained in e.g. a slow-releasing ointment or film or in a solvent such as a mouth-washing preparation. The dose of the macrolide antibiotic is preferably 0.5-10 mg/day, especially preferably 1-5 mg/day.

WO 200 602 9893 provides the use of a compound selected from the group comprising an anthraquinone and a naphtoquinone, stereoisomeric forms, racemic mixtures, metabolites, esters or salts thereof, or mixtures thereof, and/or of at least one plant extract or active fraction thereof comprising said compound for preventing and/or inhibiting biofilm formation. The present invention further relates to compositions for preventing and/or inhibiting the formation of a biofilm, oral health products and a method for preventing and/or inhibiting biofilm formation.

US 2005/0049181 A1 describes a synergistic antimicrobial composition for inhibiting biofilm formation includes an iron-sequestering glycoprotein, a cationic polypeptide and a chelating agent, or an iron-sequestering glycoprotein and a chelating agent, or an iron-sequestering glycoprotein and a cationic polypeptide. Additionally, surfactants and quaternary ammonium compounds may also be advantageously combined with iron-sequestering glycoproteins in an antimicrobial composition. Methods of using a synergistic composition for inhibiting medical device biofilm formation are also disclosed.

U.S. Pat. No. 5,718,899 relates to compositions containing a high concentration of the full repertoire of immunoglobulins, including IgA, IgM and IgG, are used to combat infections from microorganisms and viruses at a wound, surgical, or burn site, or normal tissue at time of risk of infection. The compositions can contain elevated antibody titers for several specific pathogens including *S. aureus*, CNS, Enterococci, *S. epidermidis*, *P. aeruginosa*, *E. coli*, and *Enterobacter* spp, etc. The compositions are applied directly to a wound or burn site as an ointment, creme, fluid, spray, or the like, prior to vital or bacterial attachment or biofilm formation such that adhesion of the pathogens is inhibited and the pathogens closest to the wound or burn site will be pre-opsonized for phagocytic killing prior to toxin release. The immunoglobulins in the composition can be immobilize on a biocompatible material such as collagen, fibrin, hyaluronan, biodegradable polymers, and fragments thereof, which will be placed in-situ at the wound, surgical or burn site. In addition, the immunoglobulins in the composition may be coated on the body contacting surface of an implantable device such as a catheter, contact lens, or total joint. These inventive compositions have particular application in preventing infections.

US 2004/0109852 A1 relates to methods for preventing or removing biofilm on a surface, comprising contacting the surface with an effective amount of a composition comprising one or more acylases and a carrier to degrade a lactose produced by one or more microorganisms, wherein the degradation of the lactose prevents or removes the biofilm.

U.S. Pat. No. 6,830,745 B1 describes a two component composition comprises an anchor enzyme complex to degrade biofilm structures and a second anchor enzyme component having the capability to act directly upon the bacteria for a bactericidal effect.

US 2002/0022005 A1 relates to a composition for degrading biofilm structure associated with cystic fibrosis land the debris associated therewith comprises an enzyme selected for its ability to dismantle the biofilm structure, and an anchor molecule coupled to an enzyme to form an enzyme-anchor complex. The anchor molecule is selected for its ability to attach to a surface on or proximal the biofilm structure. The attachment to the surface permits prolonged retention time of the enzyme-anchor complex where the biofilm structure and associated debris are present.

WO 02/03998 describes formulation containing between 50 and 750 mg of macrolide for delivery by aerosolization to treat infection where the bacteria is suceptible to said macrolide. This patent application also describes methods for treatment of pulmonary infections by a formulation (liquid solution, suspension or dry powder) delivered as an aerosol having mass median aerodynamic diameter predominantly inferior to 1 to 5 μm.

WO2004/075874 relates to a method of treatment and prevention of acute or chronic *Pseudomonas aeruginosa* airway infections through delivery to the lung endobronchial space, including alveoli, through delivery of an inhalable formulation and consisting in the inhalation of a macrolide antibiotic alone or in combination with another antibiotic.

The problem of resistance of bacterial biofilm to classical antiinfective agents in respiratory infectious diseases remains complete. There is still a need to dispose of a safe and efficient system to destroy, disorganize or prevent the formation of such biofilms in such diseases and/or to restore the activity of antibiotic/antiinfective drugs. It is also not only desirable to degrade biofilms within a biologic system but it is also necessary to kill the bacterial cells that are released as the biofilm is undergoing degradation.

Object of the Invention

The present invention is defined in appended independent claim 1. Preferred embodiments are defined in the dependent claims.

- It is an object of the invention to provide a composition for inhalation to the lungs which contains a combination of at least an antimicrobial agent consisting in an aminoglycoside derivative and a biofilm modifyer which is a Macrolide. The composition of the invention can be in the form of a dry powder or in a liquid form, such as a suspension or a solution, or combination thereof.
- It is another object of the present invention to provide a composition for inhalation, active against biofilm, consisting in the combination of an aminoglycoside and a macrolide, wherein the concentration (weight/weight) of each active ingredient is high i.e. superior to 10% of said dry powder composition, preferably superior to 15%, more preferably superior to 20% of said composition.
- It is an object of the present invention to provide a composition for inhalation wherein the ratio (weight/weight) of the aminoglycoside and the macrolide is comprised between 0.2 and 5, preferably between 0.5 and 3, more preferably 0.8 and 2.
- It is another object of the invention to provide a composition for inhalation wherein the total amount of active drugs (antibiotic+biofilm modifyer) is comprised between 1 and 50 mg.
- It is another object of the present invention to provide a composition for direct administration to the lungs containing an antimicrobial agent and a biofilm modifyer where the antimicrobial is an aminoglycoside derivative chosen from Tobramycin, Kanamycin, Streptomycin, Gentamicin, Amikacin, Apramycin, Arbekacin, Bekanamycin, Astromycin, Dihydrostreptomycin, Framycetin, Neomycin, Netilmicin, Isepamicin, Kanamycin, Micronomicin, Sisomicin or their salts and derivatives.
- It is another object of the present invention to provide a biofilm modifyer selected from the group of macrolides such as erythromycin, Clarithromycin, Azithromycin, Roxithromycin, Erythromycin, Telithromycin, Dirithromycin, Flurithromycin, Josamycin, Kitasamycin, Midecamycin, Dalfopristin, Oleandomycin, Midecamycin, Pristinamycin, Rokitamycin, Spiramycin, Tilmicosin, Troleandomycin, Tylosin, Virginiamycin, or their salts and derivatives
- It is another object of the present invention to administer the composition of the present invention as an aerosol or a dry powder, using a generator system which is a single dose or a multidoses inhaler; dry powder inhalers are often referred to as DPI.
- It is another object of the present invention to provide a composition for inhalation containing an antiinfective agent and a biofilm modifyer, further containing acceptable pharmaceutical excipients selected from the group consisting of carbohydrates or derivatives, lipids derivatives, or other carriers but also containing sequestring (chelating agents), antioxidants, stabilizers, buffering agents, surfactants.
- It is another object of the present invention to provide a composition for inhalation containing an antiinfective agent and a biofilm modifyer wherein the carrier is a carbohydrate selected from the group of sucrose, lactose, monohydrate, lactose anhydrous dextrose or a combination thereof.
- It is another object of the present invention to provide a composition for inhalation containing an antiinfective agent and a biofilm modifyer wherein the excipients used are lipid derivatives such as cholesterol, phospholipid derivatives, fatty acid derivatives or mixtures thereof
- It is another object of the present invention to provide a composition for inhalation containing an antiinfective agent and a biofilm modifyer and a chelating agents such as edetic acid, citric acid, malic acid, or a salt thereof
- It is another object of the present invention to provide a composition for inhalation containing an antiinfective agent and a biofilm modifyer and a antioxidant agent such as derivatives of cysteine, ascorbic acid or derivatives, tocopherol derivatives, propylgallate, parabens derivatives, etc. . . .
- It is also an object of the invention to provide a composition for inhalation efficient against bacterial biofilm consisting in a combination of an antiinfectious agent which is a aminoglycoside and a biofilm modifyer which is a macrolide, further comprising other therapeutically active agents such as mucolytic, antiinflammatory, and bronchodilator.
- It is another object of the present invention to provide a composition for direct administration to the lungs comprising a combination of antimicrobial which is an aminoglycoside derivative and a biofilm modifyer which is a macrolide, allowing to decrease the side-effects and/or the drug-drug interaction, and/or allowing to increase the compliance and/or the efficacy.

BRIEF DESCRIPTION OF THE DRAWINGS

FIG. 1 illustrates the effect of tobramycin (4 μg/ml), clarithromycin (100, 200 and 500 μg/ml) and combinations of tobramycin/clarithromycin (4/100 μg/ml, 4/200 μg/ml and 4/500 μg/ml) on a 12 day biofilm of *Pseudomonas aeruginosa.*

DETAILED DESCRIPTION OF THE INVENTION

In the present patent, "biofilm modifyer" is defined as a substance able to destroy, destructure, and disorganize the biofilm and/or to prevent or slow down its formation.

For the purpose of the present invention, the terms "antimicrobial", "antiinfective", "antibacterial", and "antibiotic" are synonyms and refer to substances having a bacteriostatic and/or a bactericidal effect against a given pathogen microorganism (bacteria, fungi, virus).

The present invention discloses the increase of efficacy of antimicrobial agents in respiratory infections associated with biofilm by the synergetic combination of at least two active agents consisting of a biofilm modifyer and an antibiotic, administered by inhalation.

Basically, one antibiotic, the aminoglycoside, at least, should be active against the bacteria contained in the biofilm, while the macrolide shall act on the biofilm for instance by disorganizing it, destructuring it, inhibiting the production of alginate, etc. . . . The present invention is useful to prevent the formation of biofilm in patients but also to treat patients with a formed biofilm.

The present invention more precisely consists of a composition dry or liquid for inhalation comprising at least one antibiotic from the aminoglycoside group and one antibiotic from the macrolide group, the antibiotic from the macrolide family being active against biofilms (=biofilm modifier).

The antibiotics from the aminoglycoside group comprise, but are not restricted to: Tobramycin, Kanamycin, Streptomycin, Gentamicin, Amikacin, Apramycin, Arbekacin, Bekanamycin, Astromycin, Dihydrostreptomycin, Framycetin, Neomycin, Netilmicin, Isepamicin, Micronomicin, Sisomicin or their salts and derivatives. (see Martindale, $33^{rd}$ edition, page 111).

The macrolides from the macrolides group comprise but are not restricted to: Clarithromycin, Azithromycin, Roxithromycin, Erythromycin, Telithromycin, Dirithromycin, Flurithromycin, Josamycin, Kitasamycin, Midecamycin, Dalfopristin, Oleandomycin, Midecamycin, Pristinamycin, Rokitamycin, Spiramycin, Tilmicosin, Troleandomycin, Tylosin, Virginiamycin, or their salts and derivatives. (see Martindale, $33^{rd}$ edition, page 112).

There are significant advantages to administer the present composition of an aminoglycoside and a macrolide directly to the lungs instead of their usual route of administration i.e. most often intravenous for aminoglycoside and oral for macrolide. First, the very significantly decrease of the systemic exposure leads to the decrease of potentially very severe adverse effects of aminoglycoside (nephrotoxicity and ototoxicity) and the mild adverse effects of macrolides. Second, the inhalation avoids drug interactions that may occur for some macrolides that are metabolized through the cytochrome P450 3A4 (like clarithromycin). Those interactions may again result in important adverse effects. Third, the interaction with food is also avoided when the composition is inhaled rather than swallowed. And last but not least, the inhaled route produces very high local concentrations of the drugs where needed.

The amount of each antibiotic and their respective ratio may vary, depending to the nature of the bacterium to eradicate, the kind of biofilm and the kind of infection to treat. The amount of aminoglycoside will be, in every case, such as to provide, locally, concentrations in aminoglycoside superior to its MIC (Minimal Inhibitory Concentration) against the planktonic bacterium considered. However, the preferred ratio (w/w) aminoglycoside/macrolide in the present invention is 0.2 to 5, preferably 0.5 to 3, more preferably 0.8 to 2.

The amount of macrolide agent inhaled shall be high enough to affect, in some way, the biofilm. It has to be noted that as the effect of macrolide derivatives on the biofilm is mediated through a non-antibacterial mechanism. Therefore, the amounts required to destroy the biofilm by inhalation may be significantly lower than the one needed for antiinfective activity pre os. Also importantly, the macrolide derivative does not need to possess an antiinfective activity against the targeted microorganism to acts on the biofilm. Nevertheless, it is a another object of the present invention to provide a composition containing high concentrations (or amounts) of each of the aminoglycoside derivative and of the macrolide derivative i.e. at least more than 10%, preferably more than 15%, and more preferably more than 20% of the dry powder composition. It is indeed particularly interesting to achieve high lung doses of those therapeutic agents with the minimum amounts of inhalations because it makes the administration easier and more importantly increase the patient's compliance. It also decreases the nominal dose of each active ingredient and thus the adverse effects linked to these actives. In the present invention, the dry powder inhaler also provides a high Fine Particle Dose (FPD) and Fine Particle Function (FPF) when tested in vitro on a Multistage Liquid Impinger (MLI, Eur. Pharm, $5^{th}$ Edition, chapter 2.9.18). The FPD and FPF are the parameters that predict in vivo lung deposition. Briefly, the FPF (%) is defined as the fraction (expressed of in percent) of the nominal dose presenting a diameter inferior to 5 μm (maximum diameter of particles to be able to reach the lungs) and the Fine Particle Dose (FPD) is the amount (in mg) per inhaled unit dose composition presenting a diameter inferior to 5 μm.

High lung deposition of each active ingredient from the composition of the present invention will achieve high local concentrations of the antibiotic (generally 5 to 20 times above the Minimal Inhibitory Concentration or MIC) in order to kill the pathogens and high local concentrations of the biofilm modifyer agent in order to destroy or destructure rapidly the biofilm.

The DPI composition of the present invention provides with a FPF of at least 15% of each active ingredient in comparison to the nominal dose, preferably superior to 20%, more preferably superior to 35%.

The preferred ratio (w/w) between the active ingredients (aminoglycoside+macrolides) and the inactive ingredients in dry powder composition of the invention, is comprised from 0.2 to 90, preferably from 0.3 to 5, more preferably 0.4 to 2. Alternatively, the compositions may be free of excipient (100% of active drugs).

In a preferred embodiment of the present invention, both antimicrobial are present under the form of a dry powder for inhalation agents and are administered in a fixed combination through inhalation. Said dry powder compositions may be formulated as a single dose composition i.e. a composition to be filled individually in capsules or blisters, or as a multidose composition i.e. a composition filled in a device equipped with a reservoir containing several doses and a metering dose system.

The dry powder composition of the present invention preferably contains the aminoglycoside derivative in a micronized form and the macrolide derivative in a micronized form. For the purpose of the present invention, "micronized" means an average particle size inferior to 20 μm, preferably inferior to 10 μm and more preferably inferior to 5 μm when measured by laser diffraction for instance. The dry powder composition of the present invention may contain more than one antibiotic and more than one biofilm modifyer The dry powder composition may further contain other excipients like buffering agents, surfactants, lubricants, chelating agents or antioxydants, aminoacids. When carbohydrate is used as main inactive ingredient, it has a role of carrier. Then, the preferred process is for manufacturing the composition of the invention is a dry blending of the micronized active ingredients with the non-micronized carrier. In case of use of a non-micronized carrier, said carrier has preferably a mean particle size comprised between 50 and 250 μm, preferably between 80 and 200 μm, more preferably between 100 and 160 μm. The preferred main carrier is anhydrous lactose or lactose monohydrate but other mono-disaccharide such as dextrose, xylitol, mannitol, saccharose etc., may be used. Mixtures of two or more carriers may also be used as well as mixtures a carrier with other kinds of excipients (lubricants, surfactants, antioxidants, etc.).

The dry powder composition of the invention may contain, in addition to the main non micronized carrier described hereinabove, a second carrier which can be non-micronized or micronized. When this second carrier is micronized, the preferred mean particle size measured by laser diffraction is inferior to 20 µm, preferably inferior to 10 µm. The second carrier can be the same chemical entity as the main carrier or a different one.

The dry powder composition obtained by dry blending may further comprise excipients aimed to improve the stability of the composition, the flowability of the powder or the lung deposition of both active ingredients.

Another composition of the invention may contain in addition to the micronized aminoglycoside and the micronized macrolide, a lipid derivative or a mixture of different lipid derivatives as excipients. In this case, the preferred process consists in the spray-drying the active ingredients together with the lipid. The spray-drying process requires the use of a liquid in which the active ingredients and excipients are solubilized or in suspension. The solution or suspension is homogeneized and then spray-dried to obtain a particles in the required mean particle range i.e. <10 µm, preferably inferior to 5 µm. This spray-drying process is a well known in the pharmaceutical industry and a specific process to obtain dry powder composition may, for instance be found in EP 1 674 085 A1.

The preferred lipid excipients are either phospholipids including anionic phospholipids, cationic phospholipids, zwitterionic phospholipids and neutral phospholipids such as for example phosphatidylcholine, phosphatidylglycerol, phosphatidyl-inositol, phospatidyl-serine, or non-phospholipids such as glycerol esters (like glycerol monostearate, glycerol behenate), fatty alcohols (preferably with C16 or more), fatty acids (preferably with C16 or more), ethers of fatty alcohols, esters of fatty acids, hydrogenated oils, polyoxyethylenated derivatives and sterols like cholesterol and its derivatives. Mixtures of two or more lipid derivatives may also be used. Preferably, a combination of a phospholipid with cholesterol or a cholesterol derivative may be used in compositions of the present invention.

The lipid excipients may also be combined to other lipidic or non lipidic excipients like carbohydrate, surfactant, lubricant, antioxidant, chelating agent.

The dry powder composition of the present invention may additionally contain one or more chelating agent. The chelating agent useful for the present invention may include edetic acid (EDTA) or a salt thereof, but other chelating agent such as citric acid, malic acid or their salts may be used. The chelating agent will preferably be present at a concentration (w/w) ranging from 0.01% to 5% of the final dry powder composition. Combinations of more than one chelating agents may also be used.

The dry powder composition of the present invention may additionally contain one or more antioxidant agent. Examples of antioxidants that can be used include derivatives of cysteine like acetylcystein and its salts, glutathion, carbocystein derivatives or ascorbic acid, derivatives of tocopherol, propylgallate, BHA, BHT.

It is to be noted that the presence of either a chelating agent or an antioxidant agent, or both, may further increase the beneficial effect on the biofilm and may consequently result in a better efficiency that the contribution of aminoglycoside and macrolide without these agents.

In a second preferred embodiment, the composition can be in the form of a liquid, comprising a carrier and both antibiotics (macrolide and aminoglycoside) in suspension and/or in solution therein. Nebulizer solutions can be formulated in a similar way to injectable Macrolide solutions well-known in the art. The liquid carrier is advantageously water, or any pharmaceutically acceptable solvent, such as ethanol, dimethylsulfoxide, glycerol, propylene glycol, and mixtures thereof. The antibiotics in the liquid compositions of the present invention shall be present in the same amount ranges as defined supra for the dry powder compositions.

EXAMPLE 1

In Vitro Demonstration of the Activity of Micronized Tobramycin+Micronized Clarithromycin on *Pseudomonas aeruginosa* Biofilm Biofilms of *Pseudomonas aeruginosa*—strain PY $O_1$ were formed according to the methods described by Ceri et al, *the calgary biofilm device: new technology for rapid determination of antibiotic susceptibilities of bacterial biofilms*, Journal of clinical microbiology, pp. 1771-1776, 1999 and Abdi-Ali et al, *bactericidal activity of various antibiotics against biofilm-producing Pseudomonas aeruginosa*, International Journal of Antimicrobial Agents 27, 196-200, 2006.

PY $O_1$: is a cystic Fibrosis clinical mucoid strain of *Pseudomonas aeruginosa* received from the Erasme Hospital, Brussels.

The determination of the minimal inhibitory concentration (MIC) is performed according to the standard of NCCLS (NCCLS, Methods for dilution Antimicrobial Susceptibility Tests for bacteria that grow aerobically; approved standards, sixth edition, M7-A6, vol. 23 no. 2, January 2003.

In the present experiment, the MIC of tobramycin, clarithromycin and the combination of both antibiotics was first determined on planktonic bacteria (=probacteria i.e. free bacteria not included in a biofilm) to prove that there is no direct additive effect of the active ingredient. The MIC of tobramycin for *Pseudomonas aeruginosa* is 3.9 µg/ml. The MIC of clarithromycin for *Pseudomonas aeruginosa* could not be determined since the results showed that the bacterium is not sensitive to this antibiotic. The MIC of the combination of tobramycin and clarithromycin is found to be around 3.9 µg/ml. These results, similar to the MIC value found for tobramycin alone demonstrate that there is no additional antibiotic effect of clarithromycin on planktonic *Pseudomonas aeruginosa*.

In a first attempt to measure the antibiotic activity (MIC) of tobramycin on *Pseudomonas aeruginosa* when incorporated in a biofilm, a culture of planktonic *Pseudomonas aeruginosa* was prepared to produce a biofilm during a period of 24 hours. Upon completion of the 24 hours the MIC of tobramycin was measured using these cultures. Surprisingly, it was found that the Minimum Inhibitory Concentration (MIC) of tobramycin on a 24 hours old biofilm of *Pseudomonas aeruginosa* was similar to the activity of tobramycin of planktonic bacteria. In other words, Tobramycin is still active on such a biofilm and there is no need to add a biofilm destroying/destructuring agent.

In a second experiment using the same modus operandi as above, we measured the MIC of Tobramycin on a 12 day old *Pseudomonas aeruginosa* biofilm. This situation is much closer to the situation observed in vivo in chronic respiratory diseases like Cystic Fibrosis. In this case, tobramycin was no longer active against said *Pseudomonas aeruginosa*.

There exists thus a significant difference between a 1 day old versus a 12 days old biofilm: it appears that a biofilm is a living entity that evolutes from the native to the mature stage. Also these experiments shall warn researchers that antibiotic activity results obtained from species that form a biofilm may not be taken in consideration unless the biofilm has had sufficient time to form properly and results found in the literature have to be taken with precaution.

Effects of Tobramycin, Clarithromycin and Combinations Thereof on 12-Day Biofilm of *Pseudomonas aeruginosa*

After having shown that the number of *Pseudomonas aeruginosa* within the biofilms was stable after 12 days, the products listed in Table 1 were added to the media for the duration of 24 hours. Thereafter the biofilm was rinsed three times with a 0.01M phosphate buffer adjusted at pH 7.5 in order to remove all cells not bound to the biofilm. The microplate was then placed on ultrasonic bath at 35° C. for 5 minutes to allow the bacteria present in the biofilm to separate from such biofilm. A bacterial count was then performed (number of coloning forming unit CFU/ml). Each experience was done twice and the CFU counting was also repeated twice/experience.

Figure 1:
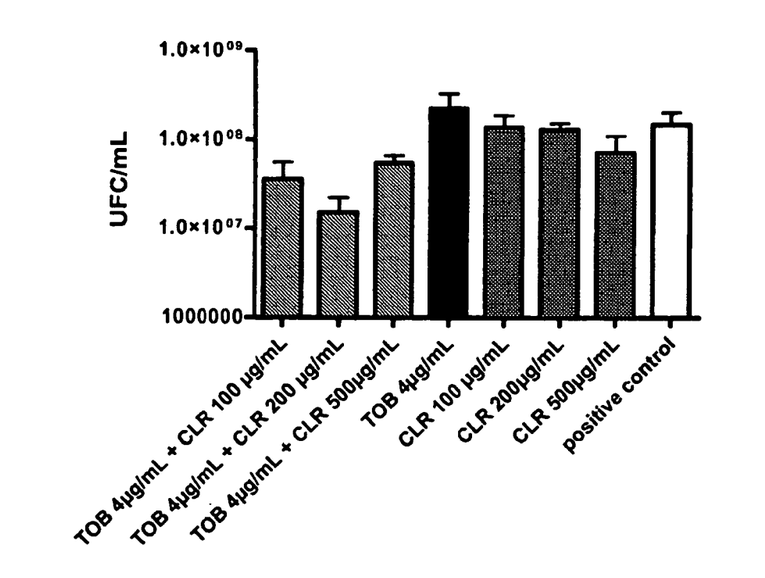

The results are shown in Table 1 and FIG. 1. It is concluded that neither tobramycin 4 µg/ml nor clarithromycin at 100, 200 and 500 µg/ml alone are able to decrease the number of CFU/ml of the 12-day biofilm versus the positive control.

TABLE 1

Effect of tobramycin (4 µg/ml), clarithromycin (100, 200 and 500 µg/ml) and combinations of tobramycin/clarithromycin (4/100 µg/ml, 4/200 µg/ml and 4/500 µg/ml) on a 12 day biofilm of *Pseudomonas aeruginosa*.

|  | PC | T 4 (µg/ml) | C 100 (µg/ml) | C 200 (µg/ml) | C 500 (µg/ml) | T/C 4/100 (µg/ml) | T/C 4/200 (µg/ml) | T/C 4/500 (µg/ml) |
|---|---|---|---|---|---|---|---|---|
| MIC (CFU × $10^7$) (Low value of MIC is desired.) | 16 | 25 | 14 | 10 | 7 | 3 | 1 | 5 |

PC: Positive control (Mueller-Hinton medium also called CAMHB)
T: Tobramycin
C: Clarithromycin
T/C: Combination Tobramycin/Clarithromycin To the contrary all the combinations of Tobramycin/Clarithromycin were able to decrease the number of CFU/ml originated from the biofilm of *Pseudomonas aeruginosa* with a maximal effect being observed for the combination TOBRAMYCIN 4 µg/ml+CLARITHROMYCIN 200 µg/ml which shows a number of CFU/ml of about $10^7$ while tobramycin alone at 4 µg/ml shows a number of CFU/ml of around $2.5 \times 10^8$. This means a more than 25 times decrease in the number of CFU/ml for the combination versus the reference product tobramycin.

It can be seen that enhanced results are determined when at least 100 µg/ml clarithromycin is combined with tobramycin, preferably at least 200 µg/ml. The efficacy of the mixture decreases somehow for concentration in clarithromycin grater than 500 µg/ml.

EXAMPLE 2

A dry powder composition for inhalation of tobramycin and clarithromycin was formulated using micronized tobramycin supplied by Teva Plantex (Israël). Clarithromycin was supplied by Teva Plantex (Israel) in a non-micronized form. Clarithromycin was then micronized using the micronizer MC-one® (JetpHarma, Switerland). To obtain a product with particle size suitable to reach the respiratory tract (i.e. 80% of particles inferior to 10 µm, and 90% of particles inferior to 5 µm when measured by laser diffraction). The micronisation parameters were a pressure of 10 bars in the Venturi, a pressure of 8 bars in the ring and a feeding rate of 5 g/minute. The mean particle size of the micronized clarithromycin obtained (measured by laser diffraction) was 1.6 µm.

Manufacturing of DPI Composition:

400 g of anhydrous lactose (100-160 µm) were put in a planetary mixer together with 50 g of micronized lactose monohydrate. The two lactoses were blended at 40 rpm for 10 minutes. 200 g of micronized tobramycin and 100 g of micronized clarithromycin were added to the mix of lactoses using the "sandwich technique", i.e. by alternating the layer of lactoses and the layer of active ingredients to obtain a final mix as homogeneous as possible. The mix was blended for 10 minutes at a speed of 40 rpm.

Samples were taken from this powder blend to assure both active ingredients were homogeneously blended. 50 mg of the powder mix was then filled into number 3 hydroxypropylmethylcellulose (HPMC) capsules. These capsules are ready for use with a dry powder inhaled device such as the MIAT monodose inhaler, or any other suitable capsule based inhalation device.

EXAMPLE 3

Edetic acid in an amount of 0.5% (weight/weight) was added to the blend of example 2. The powder was thereafter filled in a Miat multidose inhaler device.

EXAMPLE 4

400 g of anhydrous lactose (100-160 µm) was introduced in a planetary mixer and 150 g of micronized tobramycin, 150 g of micronized clarithromycin and 20 g of N-acetylcysteinate lysine (as antioxidant) were added using the "sandwich technique", i.e. by alternating the layer of lactose and the layer of active ingredients to obtain a final blend as homogeneous as possible. The blend was mixed for 10 minutes at a speed of 40 rpm. The blend was then filled in size 3 hard gelatine capsules (40 mg of powder/capsule).

EXAMPLE 5

10 g of micronized tobramycin, 5 g of clarithromycin were dissolved in a 80/20 (w/w) water/ethanol mixture. 300 mg of Phospholipon 90H® and 1.2 g of cholesterol were added and dissolved in said solution containing the active ingredients. The solution was thereafter spray-dried to obtain a powder consisting of micrometric spherical lipidic particles with a very high content in active ingredients. This powder was filled in HPMC capsules for inhalation (20 mg of powder/capsule).

EXAMPLE 6

400 g of anhydrous lactose (100-160 µm) was mixed in a planetary mixer (40 rpm for 10 minutes) with 200 g of micronized tobramycin and 200 g of micronized clarithromycin. 40 mg of the blend obtained was filled into size 3 hydroxypropylmethylcellulose capsules. This produced capsules each containing 10 mg of micronized tobramycin and 10 mg of micronized clarithromycin that may be used for inhalation In Vitro Lung Deposition The determination of the Fine Particle Fraction (FPF) i.e. the fraction (expressed in percent) of the nominal dose presenting a diameter inferior to 5 μm (maximum diameter to reach the lungs) and the Fine Particle Dose (FPD) i.e. the amount (in mg) per capsule presenting a diameter inferior to 5 μm, has been performed on the capsules using the Axahaler device as powder inhaler device. The in vitro lung deposition test was performed using equipment and conditions as described in the European Pharmacopoeia (5$^{th}$ edition, chapter 2.9.18—apparatus C). This equipment consists of a Multistage Liquid Impinger (MLI) and was operated with an air flow of 100 L/min during a period of time of 2.4 seconds to simulate inhalation capabilities of patients. The quantification of the deposition of each drug on each stage of the MLI was performed by HPLC equipped with a a Corona detector. The results are presented in Table 2.

TABLE 2

FPF (%) and FPD (mg) obtained with the compositions of example 6 (MLI 100 L/min) containing 10 mg of tobramycin and 10 mg of clarithromycin/capsule (n = 3)

|  | MLI1 (mg) | MLI2 (mg) | MLI3 (mg) | Mean (mg) | SD |
|---|---|---|---|---|---|
| Tobramycin (mg) |  |  |  |  |  |
| Device | 1.035 | 0.938 | 1.272 | 1.082 | 0.17 |
| Throat | 0.929 | 0.859 | 0.771 | 0.853 | 0.08 |
| Stage 1 | 1.760 | 1.837 | 1.546 | 1.714 | 0.15 |
| Stage 2 | 0.614 | 0.726 | 0.606 | 0.648 | 0.07 |
| Stage 3 | 1.512 | 1.818 | 1.895 | 1.742 | 0.20 |
| Stage 4 | 1.598 | 1.965 | 2.202 | 1.922 | 0.30 |
| Filter | 0.664 | 0.838 | 0.778 | 0.760 | 0.09 |
| FPD (mg) | 3.60 | 4.45 | 4.72 | 4.26 | 0.59 |
| FPF (mg) | 35.96 | 44.50 | 47.20 | 42.55 | 0.06 |
| Clarithromycin (mg) |  |  |  |  |  |
| Device | 1.155 | 1.048 | 1.433 | 1.212 | 0.20 |
| Throat | 1.025 | 1.134 | 1.223 | 1.127 | 0.10 |
| Stage 1 | 1.338 | 1.566 | 1.352 | 1.419 | 0.13 |
| Stage 2 | 0.664 | 0.845 | 0.680 | 0.729 | 0.10 |
| Stage 3 | 1.715 | 1.891 | 2.078 | 1.895 | 0.18 |
| Stage 4 | 1.162 | 1.482 | 1.533 | 1.392 | 0.20 |
| Filter | 0.478 | 0.598 | 0.574 | 0.550 | 0.06 |
| FPD (mg) | 3.14 | 3.76 | 3.98 | 3.63 | 0.44 |
| FPF (mg) | 31.37 | 37.56 | 39.85 | 36.26 | 0.04 |

The FPF of tobramycin and clarithromycin obtained are 42.5% and 36.3% respectively. The FPD/capsule of tobramycin and clarithromycin are 4.26 mg and 3.63 mg respectively. Those results clearly demonstrate that the compositions of the invention allow to reach very high lung deposition of both the antibiotic and the biofilm modifyer. Such high lung deposition is suitable for use in vivo. Indeed, the volume of epithelial liquid in the lung is generally estimated at about 100 ml. and lung deposition results show that each capsule of the composition of example 6 allows thus to obtain a lung concentration of respectively 42.6 μg/ml of tobramycin and 36.3 μg/ml of clarithromycin.

EXAMPLE 6

Different compositions (F1 to F5) were manufactured using the blending process as described in example 6.

| Active Ingredient | mg/dry powder composition | | | | |
|---|---|---|---|---|---|
|  | F1 | F2 | F3 | F4 | F5 |
| Tobramycin base | 20 | / | 5 | 15 | 5 |
| Amikacine | / | 15 | 5 | / | / |
| Clarithromycin | 10 | 10 | 15 | / | 5 |
| Azithromycin | / | / | / | 10 | / |
| Anhydrous lactose | 20 | 25 | 20 | 20 | 10 |
| Total weight/composition | 50 | 50 | 45 | 45 | 20 |

What is claimed is:

1. A mature biofilm-modifying, antibacterial inhalation composition for the treatment of lung disease caused by bacteria contained in in a mature biofilm, comprising at least:
   (a) tobramycin or a pharmaceutically-acceptable salt thereof, and
   (b) a biofilm modifier which is a macrolide selected from the group consisting of azithromycin, clarithromycin and erythromycin; or a pharmaceutically-acceptable salt thereof or both;
   said components (a) and (b) being present in a weight ratio (a)/(b) of from about 1/125 to 1/25 to disrupt said mature biofilm and treat said disease.

2. The composition of claim 1, which is in a form of a dry powder.

3. The composition of claim 1, which is in a form of a suspension or a solution.

4. The composition of claim 1, wherein a total amount of active ingredients represents more than 20% of the composition.

5. The composition of claim 4, wherein the total amount of the active ingredients represents more than 30% of the composition.

6. The composition of claim 5, wherein the total amount of the active ingredients is more than 40% of the composition.

7. The composition of claim 1, further containing at least one or more pharmaceutically-acceptable excipients for inhalation to the lungs.

8. The composition of claim 7, wherein said at least one of said pharmaceutically-acceptable excipients is a carbohydrate or a mixture of two or more carbohydrates.

9. The composition of claim 8, wherein at least one of said pharmaceutically-acceptable carbohydrate comprises anhydrous lactose, lactose monohydrate, mannitol, xylitol, dextrose, saccharose, a cyclodextrin compound or a mixture thereof.

10. The composition of claim 7, wherein said at least one of said pharmaceutically-acceptable excipients is a lipidic excipient.

11. The composition of claim 10, wherein at least one of said lipidic excipients is selected from the group consisting of cholesterol compounds, phospholipids, ethers of fatty acids, esters of fatty acids, hydrogenated oils, polyoxyethylenated compounds and esters of glycerol.

12. The composition of claim 11, wherein said composition contains a mixture of cholesterol and a phospholipid or a cholesterol compound and a phospholipid phospholipid.

13. The composition of claim 1, further containing one or more antioxidant(s) comprising cysteine and or esters thereof, ascorbic acid and/or salts thereof, tocopherol esters, propylgallate, butylhydroxyanisole, or butylhydroxytoluene.

14. The composition of claim 1, wherein the macrolide compound is clarithromycin or a salt thereof, said composition being free of another microbial compound.

15. The composition of claim 1, wherein said composition is free of excipients.

16. The composition of claim 2, wherein said dry powder composition is filled in pharmaceutically-acceptable capsules.

17. The composition of claim 16, wherein said pharmaceutically-acceptable capsules comprise, as a main polymer, gelatin, hydroxypropylcellulose or starch.

18. The composition of claim 2, wherein said dry powder is filled into a multidose dry powder inhaler system.

19. The composition of claim 1, which is contained in a nebulizer container.

20. The composition of claim 1, wherein said components (a) and (b) are present in a weight ration (a/b) of about 1/50.

21. The composition of claim 20, wherein said component (b) is clarithromycin or a pharmaceutically-acceptable salt thereof.

* * * * *